United States Patent [19]
Song et al.

[11] Patent Number: 6,046,312
[45] Date of Patent: Apr. 4, 2000

[54] WATER SOLUBLE AZO DYES AND THEIR SYNTHESIS AND USE

[75] Inventors: Han-chul Song; Kwang-nak Koh; Shin-won Kang; Jin-ho Cho; Joohg-hun Kim; Su-mi Lee, all of Kwangyokshi, Rep. of Korea

[73] Assignee: Dongil Technology Ltd., Kyonggi-do, Rep. of Korea

[21] Appl. No.: 09/436,865

[22] Filed: Nov. 9, 1999

[30] Foreign Application Priority Data

Aug. 12, 1999 [KR] Rep. of Korea ................. 99/33013

[51] Int. Cl.⁷ .................. C09B 29/036; C09B 29/09; G01N 33/52
[52] U.S. Cl. .............................. 534/770; 436/95
[58] Field of Search ................. 534/770; 436/95

[56] References Cited

U.S. PATENT DOCUMENTS

5,298,608  3/1994  Murayama et al. ............... 534/790 X

OTHER PUBLICATIONS

Koumoto et al., Chemical Abstracts, 130:89807, 1998, "Design of a Visualized Sugar Sensing System Utilizing a Boronic Acid–Azopyridine Interaction".

*Primary Examiner*—Fiona T. Powers
*Attorney, Agent, or Firm*—Darby & Darby

[57] ABSTRACT

Disclosed are water soluble azo dyes, represented by Formula I or II, and their synthesis and use. The water soluble azo dyes are synthesized by diazotizing 4-aminopyridine and coupling the resulting diazo intermediate with alkylated metanilic or orthanilic acid. To be suitable for measuring blood glucose levels, the dyes are combined with m-nitrophenyl boronic acid in an aqueous solvent. A combined ao form of the dyes with glucose shows a peak at 540 nm. At this wavelength, the absorptivity has a tendency to increase with the increasing of glucose level, which allows the measurement of blood glucose levels.

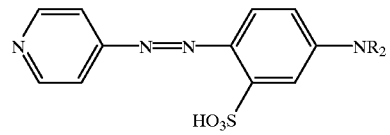

(I)

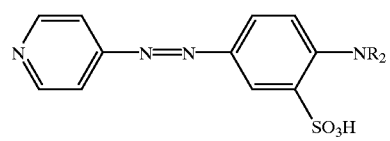

(II)

wherein R has a 1–4 carbon atom length and is an alkyl, a hydroxy alkyl, a carboxyl-containing alkyl, or a sulfonyl-containing alkyl.

10 Claims, 2 Drawing Sheets

WATER SOLUBLE AZO DYES AND THEIR SYNTHESIS AND USE

BACKGROUND OF THE INVENTION

1. Field of the invention

The present invention relates to water soluble dyes useful in measuring the glucose levels in an aqueous solution. Also, the present invention is concerned with the synthesis and use of such water soluble dyes.

2. Description of the Prior Art

Measurement of blood glucose levels is very important as basic data for diagnosing and treating diabetics and controlling the meals of diabetic patients. Blood Glucose concentrations have been measured by several methods and they were well known to those skilled in the art.

U.S. Pat. No. 5,605,152 discloses a sensor, composed of optical fibers, which is implanted within a vein of a patient suffering from diabetes, to measure his or her blood glucose levels. The sensor comprises an optode coated with glucose oxidase which oxidizes glucose into gluconic acid and hydrogen peroxide in the presence of oxygen. Blood glucose levels are indirectly detected by measuring the amount of oxygen consumed when the glucose in blood is oxidized. This measuring method, although found to be of somewhat high accuracy, suffers from a disadvantage of being applicable only to the patients who are treated periodically over a long period of time in specialized places, for example, hospitals, because they always carry the sensor within their veins.

Therefore, there remains a need for sensors of measuring blood glucose levels, which are easy to carry with and convenient for the patients slightly suffering from diabetics to use.

A glucose sensor which meets such requirements is found in U.S. Pat. No. 5,779,867. In this patent there is disclosed a self contained glucose sensor which comprises two strip type glucose sensing electrodes the potential differences between which are used to measure blood glucose levels. Of the two glucose sensing electrodes, one has an active surface comprising an organic conducting redox salt dispersed in a polymeric membrane, with the membrane coating a conductive strip while the other is a strip type Ag/AgCl reference electrode having its active surface separated from physical contact with the strip type glucose sensor. Between the two electrodes is filled a carrier strip of water absorbent paper or film which contains an enzyme system and an oxidizable dye. This sensor is capable of measuring a relatively low concentration of glucose and keeping constant the potential differences according to glucose levels, thereby detecting glucose levels with high accuracy. However, a significant disadvantage is an economical unfavorableness because the electrodes, relatively expensive, must be discarded after they are used once.

U.S. Pat. Nos. 5,059,394 and 5,179,005 disclose glucose sensing apparatuses having glucose sensing chambers which comprise glucose oxidase, peroxidase and dye capable of reacting with hydroperoxide to cause a color change. When glucose is oxidized by the glucose oxidase, hydroperoxide is formed which reacts with the dye, causing a color change which is used to measure the blood glucose level with the aid of an optical sensor. This technique is disadvantageous in that it has a very large error margin up to about 10% owing to the fact that many reaction steps are required to obtain results for glucose levels.

The above conventional methods are of indirect measurement rather than direct measurement.

SUMMARY OF THE INVENTION

While referring to various records to design a system which is able to measure blood glucose levels through direct reaction with glucose, the present inventors took notice of a Koumoto report.

Koumoto et al., reported in Supramolecular Chemistry 9, 203 (1998) their experiment results which are summarized as follows: when phenylboronic acid substituted with a nitro group reacts with saccharides, such as ribose, mannose, fucose, xylose, arabinose, fructose and ramnose, to form an ester, this boron compound is increased in acidity and when pyridine ring-containing dyes, which are of basicity, perform a Lewis acid-base reaction with boronic acid, their colors are changed depending on the acidity of the boronic acid.

In this article, while a solution of such a dye, water-insoluble, in an inorganic solvent, such as methanol, was reacted with the saccharides, a measurement was made of the absorption spectrum of the dye. The absorptivity was found to show a constant change in accordance with the concentration of the saccharides.

However, this technique, as it is, cannot be applied for the measurement of blood concentration levels because the water-insoluble dyes are not dissolved in blood.

Knowledge of photochemical process allows modification and adaptation leading to this invention.

Based on the report of the Koumoto et al., the intensive and thorough research on measurement of blood glucose levels, repeated by the present inventors aiming to develop a measuring system which is accurate and convenient for use, resulted in the finding that introduction of water-soluble functional groups into the dyes is possible and makes them soluble in water, thereby allowing the direct measurement of blood glucose levels.

Therefore, it is an object of the present invention to overcome the above problems encountered in prior arts and to provide a dye which is soluble in water and can react with boronic acid, changing in color with the acidity of the boronic acid.

It is another object of the present invention to provide a method for synthesizing a dye which is changed in color as a result of the reaction with glucose in aqueous solutions. It is a further object of the present invention to provide a method for measuring glucose levels in aqueous solutions.

In an aspect of the present invention, there is provided a water-soluble azo compound represented by the following general formula I or II:

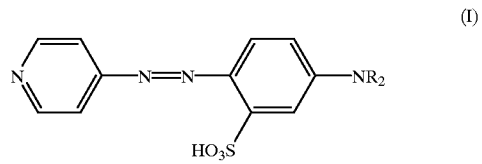

(I)

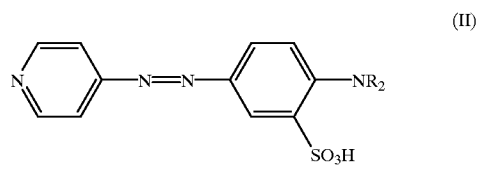

(II)

wherein R has a 1–4 carbon atom length and is an alkyl, a hydroxy alkyl, a carboxyl-containing alkyl, or a sulfonyl-containing alkyl.

In another aspect of the present invention, there is provided a method for preparing a water soluble azo compound of Formula I or II, comprising the steps of: diazotizing 4-aminopyridine to give a diazo intermediate; coupling the diazo intermediate with an alkylated metanilic or orthanilic acid to form a dye; and purifying the dye through salting-out.

In a further aspect of the present invention, there is provided a composition for measuring glucose levels in an aqueous solution, comprising an azo compound of claim 1 or 2 and a boronic acid compound represented by the following Formula III in water:

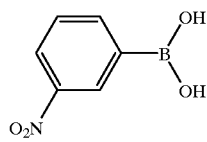

(III)

at a molar ratio of the boronic acid to the azo compound from 50 to 150.

In still a further aspect of the present invention, there is provided a method for measuring glucose levels in aqueous solutions, in which the composition is reacted with an aqueous glucose solution and the composition is measured for absorbance at a wavelength of 500–560 nm.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
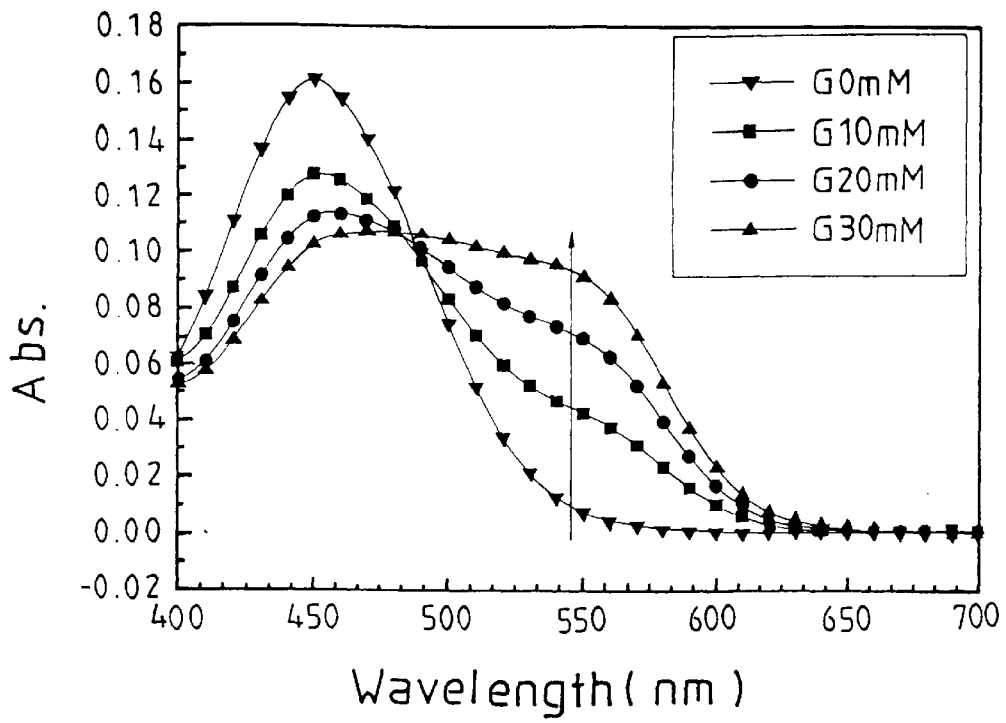
FIG. 1 is a graph showing absorption spectra of an azo solution according to an embodiment of the present invention, depending on the glucose levels in an aqueous solution.

Details are given of the present invention, below.

In the present invention, blood glucose levels are measured by taking advantage of the reaction between an azo compound containing pyridine rings, represented by the following general Formula I or II and a boronic acid represented by the following general Formula III:

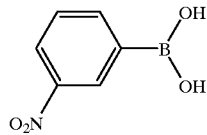

(III)

wherein R has a 1–4 carbon atom length and is an alkyl, a hydroxy alkyl, a carboxyl-containing alkyl, or a sulfonyl-containing alkyl. When the pyridine-containing azo compound of Formula I or II is reacted with the boronic acid of Formula III, they interact mutually to form an adduct represented by the following Formula IV:

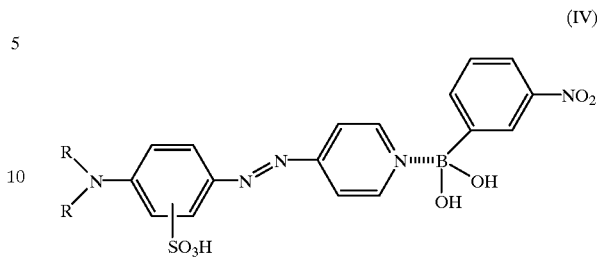

(IV)

wherein R is as defined above.

The interaction is a kind of Lewis acid-base reaction in which the nitrogen composing the pyridine ring of the azo chromophore behaves as a base, providing an unshared pair of electrons while the boron which has an incompletely filled valence shell acts like an acid. If 1,2-diols, such as glucose, are present along with the adduct, glucose binds to the boronic acid moiety via two ester linkages as shown in the following chemical Formula V:

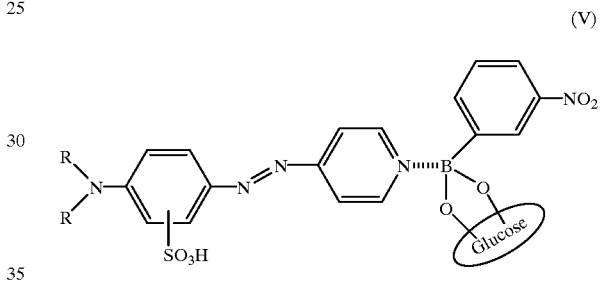

(V)

wherein R is as defined above.

The boronate thus formed is of higher Lewis acidity than is the boronic acid, so that the pyridine ring composing the dye shows an electron withdrawing effect, leading to a change in the absorption band of the dye.

The compound of Formula I, which is an object of the present invention, can be prepared by diazotizing 4-aminopyridine, able to do acid-base reaction with boronic acid, followed by coupling the resulting diazo intermediate with alkylated metanilic acid. For the compound of Formula II, alkylated orthanilic acid is used to couple with the diazo intermediate resulting from the diazotization of 4-aminopyridine. The diazotization is conducted by reacting 4-aminopyridine with sodium nitrite at 0–5° C. in the presence of an acid, such as hydrochloric acid, sulfuric acid, phosphoric acid or a mixture of sulfuric acid-acetic acid-propionic acid. In order to accomplish the coupling reaction, the alkylated metanilic acid or the alkylated orthanilic acid is dispersed in water and slowly added with the diazo intermediate while the reaction is adjusted to pH 3–5 by use of NaOH.

After completion of the diazotization and coupling reaction, the product, that is, the dye of Formula I or II, can be isolated by a salting-out process, but not by chromatography. Useful salts for the salting-out are KCl and NaCl. To obtain pure dye from the inorganic salt mixture of the dye obtained after the salting-out, the mixture is dried and washed by a polar solvent, such as ethanol, methanol or acetone.

To be suitable for measuring blood glucose levels, the dye is combined with the compound of Formula III in an aqueous solvent. In the resulting mixture solution, the concentrations of the components may be appropriately controlled depending on the absorption wavelength or absorptivity intended to be measured. When the mixture solution comprises the dye I or II at a concentration of $1 \times 10^{-5} - 1 \times 10^{-4}$ moles/L and the compound III at a concentration of $5 \times 10^{-4} - 1.5 \times 10^{-3}$, preferable absorptivity tendency may be obtained. In order to increase the solubility of the compound of Formula III, water is added. Alternatively, a polar solvent may be used at an amount of 0–10%. A buffer solution may be useful to adjust the acidity of the mixture solution into pH 7.4, the acidity of blood. The existence of glucose in the mixture solution makes a new absorption band. In this band, the absorptivity has a tendency to increase with the increasing of glucose level.

A better understanding of the present invention may be obtained in light of the following examples which are set forth to illustrate, but are not to be construed to limit the present invention.

EXAMPLE I

A compound of Formula I (R=ethyl) was synthesized as follows:

In a 3-neck flask were charged 10.42 g of aniline-3-sulfonic acid, 24.0 g of $NaHCO_3$ and 20.0 ml of water which were stirred until carbon dioxide was generated up. When carbon dioxide was generated no more, the 3-neck flask was equipped with a condenser and a dropping funnel and heated to 100° C., after which 24.6 ml of diethyl sulfate was fed into the flask over a 2 hour period, followed by stirring at 100° C. for 2 hours to complete the reaction. N,N-diethylaminobenzene-3-sulfonic acid, thus obtained, was used for the next reaction without being further purified.

Separately, 36 ml of sulfuric acid was placed in a flask, cooled to 0° C. and added with 4.97 g of $NaNO_3$ to produce nitrosyl sulfonic acid while being stirred with the aid of a mechanical stirrer. To this, then, a solution of 5.65 kg of 4-aminopyridine in 12 ml of acetic acid and 46 ml of propionic acid was added at 0–5° C. to produce a diazonium salt of 4-aminopyridine.

In a flask was charged the previously synthesized N,N-diethylaminobenzene-3-sulfonic acid which was adjusted to pH 4.6–4.7 and then, slowly added with the diazonium salt at 0–5° C. to synthesize the dye of Formula I. This was subjected to salting-out to obtain solid precipitates containing NaCl and $Na_3SO_4$. Recrystallyzation of the solid precipitates in methanol afforded a pure form of the compound of Formula I at a yield of 65%.

EXAMPLE II

The same procedure as in Example I was repeated, except that aniline-2-sulfonic acid was used instead of aniline-3-sulfonic acid, to synthesis a compound of Formula II (R=ethyl). The synthesized product was isolated through salting-out and recrystallization. Yield 60%.

EXAMPLE III

A compound of Formula I (R=ethyl) and a compound of Formula III were mixed as follows:

A phosphate buffer (pH 7.4) was added to a mixture comprising 0.04 g of the compound of Formula I and 0.167 g of the compound of Formula III (m-nitrophenylboronic acid) to a total volume of 1,000 ml and then, well stirred.

EXAMPLE IV

A phosphate buffer (pH 7.4) was added to a mixture comprising 0.2 g of a compound of Formula I (R=ethyl) and 0.84 g of a compound of Formula III (m-nitrophenylboronic acid) to a total volume of 1,000 ml and then, well stirred.

EXPERIMENTAL EXAMPLE I

To the solution obtained in Example III, glucose was added to a concentration of 10, 20 and 30 mM. From these resulting solutions, absorption spectra were taken, and the results are shown in FIG. 1.

Figure 2:
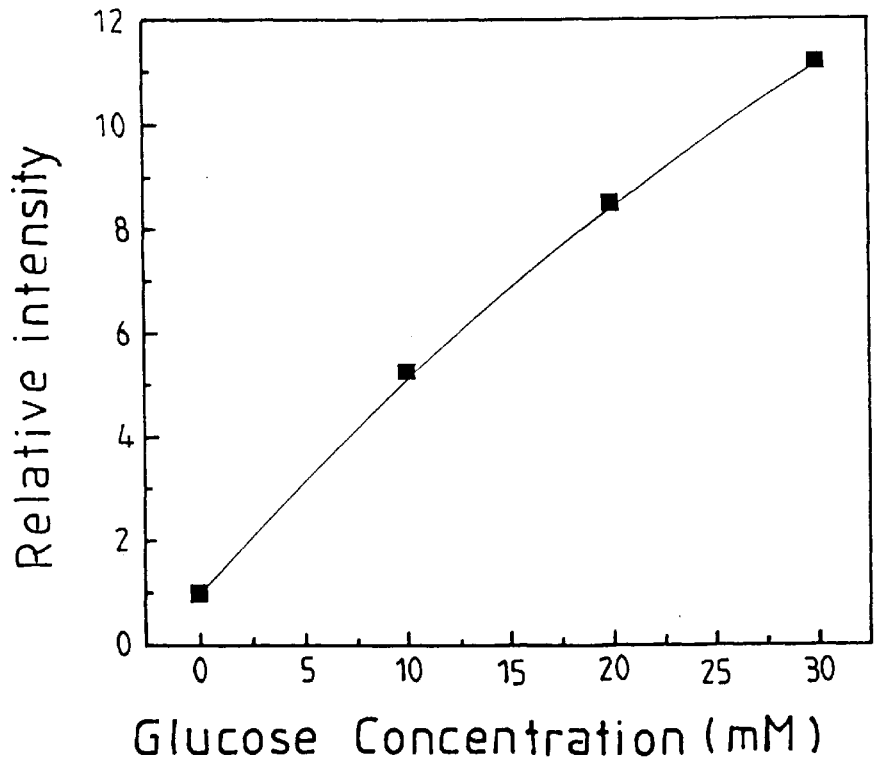
FIG. 2 is a graph showing the relative intensity at 540 nm according to the glucose levels in an aqueous solution.

When no glucose was added, the solution was tinged with yellow with a maximum of absorbance read at a wavelength of 450 nm, as seen in FIG. 1. As the glucose concentration of the solution was increased form 0 mM to 10 mM, then to 20 mM and finally to 30 mM, a new absorption band sprang forth at 540 nm while the color of the solution was changed from yellow to purple as easily detected by the naked eye. The relative intensity of the absorption spectra at 540 nm was plotted with regard to glucose concentrations and the result is given in FIG. 2.

EXPERIMENTAL EXAMPLE II

To the solution obtained in Example IV, glucose was added to a concentration of 10, 20 and 30 mM. From these resulting solutions, absorption spectra were taken, and the results are shown in FIG. 3.

Figure 3:
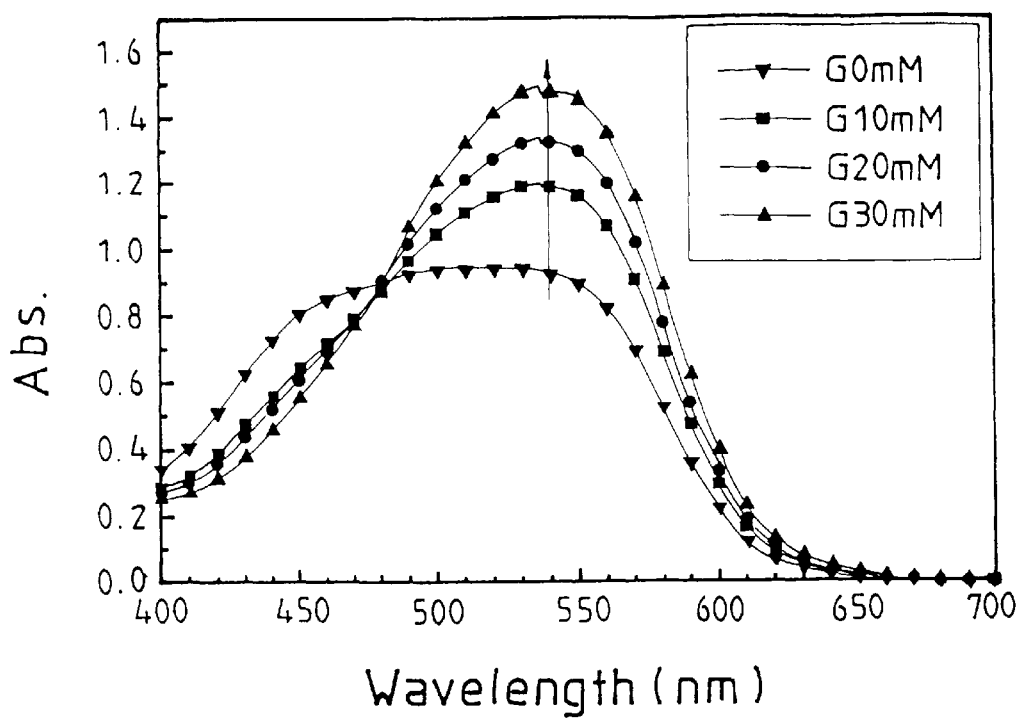
FIG. 3 is a graph showing absorption spectra of an azo solution according to an embodiment of the present invention, depending on the glucose levels in an aqueous solution.
Figure 4:
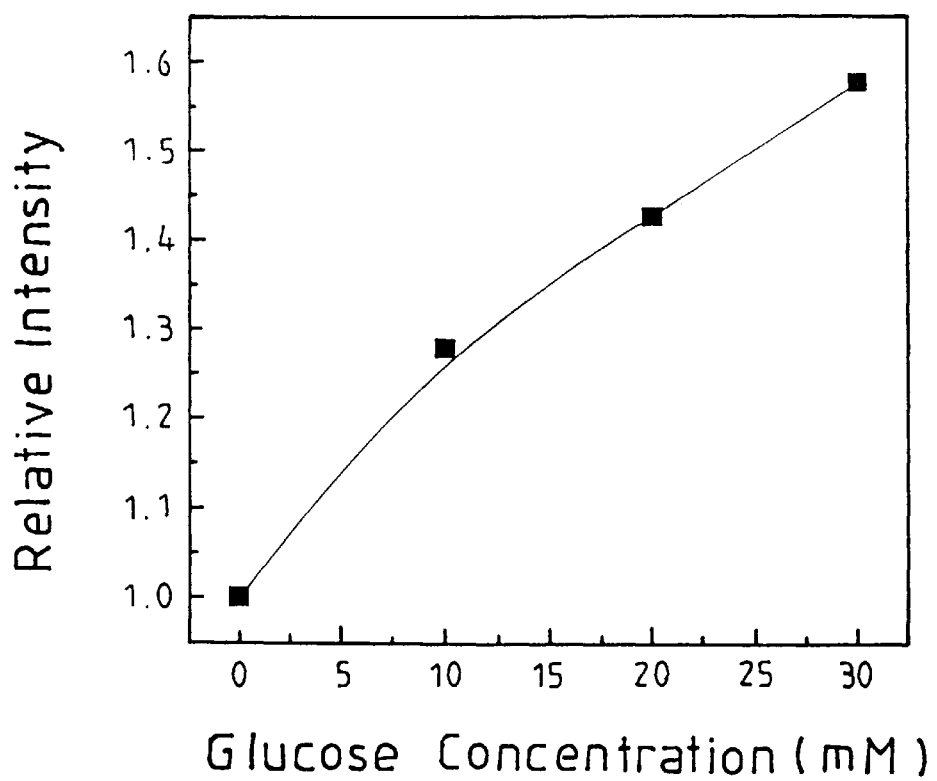
FIG. 4 is a graph showing the relative intensity at 540 nm according to the glucose levels in an aqueous solution.

When no glucose was added, the solution was tinged with yellow while a maximum of absorbance was read at a wavelength of 450 nm, as seen in FIG. 3. As the glucose concentration of the solution was increased from 0 mM to 10 mM, then to 20 mM and finally to 30 mM, a new absorption band sprang forth at 540 nm with a color change from yellow to purple as easily detected by the naked eye. The relative intensity of the absorption spectra at 540 nm was plotted with regard to glucose concentrations and the result is given in FIG. 4.

As described hereinbefore, the dyes according to the present invention are far superior to conventional ones (e.g., Kuomoto et al., Supramolecular Chemistry 9, 203 (1998)) in water solubility. Thus, the dyes according to the present invention are very useful to measure blood glucose levels with ease. In addition, by virtue of their direct reaction with glucose, the dyes make sure of an accurate measurement for blood glucose levels.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A water soluble azo compound, represented by the following general Formula I:

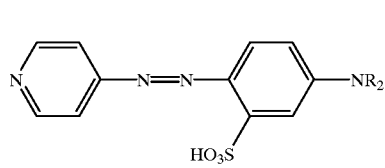

(I)

wherein R has a 1–4 carbon atom length and is an alkyl, a hydroxy alkyl, a carboxyl-containing alkyl, or a sulfonyl-containing alkyl.

2. A water soluble azo compound, represented by the following general Formula II:

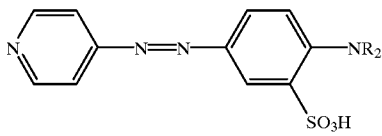

wherein R has a 1–4 carbon atom length and is an alkyl, a hydroxy alkyl, a carboxyl-containing alkyl, or a sulfonyl-containing alkyl.

3. A method for preparing a water soluble azo compound represented by the following general Formula I:

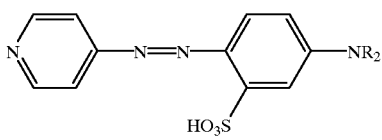

wherein R has a 1–4 carbon atom length and is an alkyl, a hydroxy alkyl, a carboxyl-containing alkyl, or a sulfonyl-containing alkyl, comprising the steps of:
  diazotizing 4-aminopyridine to give a diazo intermediate;
  coupling the diazo intermediate with an alkylated meta-nilic acid to form a dye; and
  purifying the dye through salting-out.

4. A method for preparing a water soluble azo compound represented by the following general Formula II:

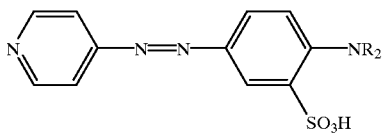

wherein R has a 1–4 carbon atom length and is an alkyl, a hydroxy alkyl, a carboxyl-containing alkyl, or a sulfonyl-containing alkyl, comprising the steps of:
  diazotizing 4-aminopyridine to give a diazo intermediate;
  coupling the diazo intermediate with an alkylated ortha-nilic acid to form a dye; and
  purifying the dye through salting-out.

5. A method as set forth in claim 3 wherein said diazotizing step is carried out by reacting 4-aminopyridine with sodium nitrite at 0–5° C. in the presence of an acid selected from the group consisting of hydrochloric acid, sulfuric acid, phosphoric acid and a sulfuric acid-acetic acid-propionic acid mixture.

6. A method as set forth in claim 3 wherein said coupling step is carried out by dispersing the alkylated metanilic or orthanilic acid at 0–5° C. in water and slowly adding the diazo intermediate to the alkylated metanilic or orthanilic acid solution while the solution is adjusted to pH 3–5 with an NaOH solution.

7. A method as set forth in claim 3 wherein said purifying step is carried out by salting-out the dye with KCl or NaCl to give an addition salt of the dye and washing the addition salt with a polar organic solvent selected from the group consisting of ethanol, methanol and acetones.

8. A composition for measuring glucose levels in aqueous solutions, comprising an azo compound of claim 1 and a boronic acid compound represented by the following Formula III in water:

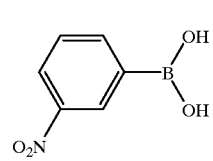

at a molar ratio of the boronic acid to the azo compound from 50 to 150.

9. A composition as set forth in claim 8, wherein said mixture is controlled to pH 7.4 with a buffer.

10. A method for measuring glucose levels in aqueous solutions, in which a composition of claim 8 is reacted with an aqueous glucose solution and the composition is measured for absorbance at a wavelength of 500–560 nm.

* * * * *